United States Patent [19]
Sjöquist

[11] 3,995,018
[45] Nov. 30, 1976

[54] METHOD OF BINDING IMMUNOGLOBULIN EMPLOYING A POLYPEPTIDE FROM MICROORGANISMS

[75] Inventor: John Axel Sjöquist, Uppsala, Sweden

[73] Assignee: Pharmacia Aktiebolag, Uppsala, Sweden

[22] Filed: Oct. 25, 1973

[21] Appl. No.: 409,572

[30] Foreign Application Priority Data

Nov. 6, 1972 Sweden............................ 14330/72
Feb. 8, 1973 Sweden.............................. 7301779

[52] U.S. Cl............................ 424/1.5; 260/112 R; 424/7; 424/12; 424/88
[51] Int. Cl.² .................... G01N 33/00; C07G 7/00; A61K 39/00; A61K 43/00
[58] Field of Search .................... 424/1, 12, 88, 359

[56] References Cited
UNITED STATES PATENTS 3,555,143  1/1971  Axen et al. ............................. 424/1
3,788,948  1/1974  Kagedal et al. ..................... 424/1 X
3,790,663  2/1974  Garrison et al. ...................... 424/12
3,850,798  11/1974  Sjoquist............................ 210/31 C

FOREIGN PATENTS OR APPLICATIONS 7,018,879  6/1970  Japan................................... 424/12

OTHER PUBLICATIONS

Bambardieri et al., Proc. Soc. Exp. Biol. Med., vol. 133, No. 4, Apr. 1970, pp. 1366–1369.

Primary Examiner—Benjamin R. Padgett
Assistant Examiner—Christine M. Nucker
Attorney, Agent, or Firm—Fred Philpitt

[57] ABSTRACT

A method of binding, in the presence of a liquid, at least one immunoglobulin or its free Fc-fragment, the immunoglobulin being in free form or with its Fab-part bound to an antigen to which is optionally in turn bound one or more groups or substances, to a polymer insoluble in said liquid with the assistance of a substance attached to the polymer. The substance used is at least one polypeptide from microorganisms to which polypeptide the Fc-part of the immunoglobulin or its free Fc-fragment can bind itself.

11 Claims, No Drawings

METHOD OF BINDING IMMUNOGLOBULIN EMPLOYING A POLYPEPTIDE FROM MICROORGANISMS

The present invention relates to a method of binding, in the presence of a liquid, at least one immunoglobulin or its free Fc-fragment, the immunoglobulin existing in free form or with its Fab-part bound to an antigen to which is optionally bound one or more groups or substances, to a polymer which is insoluble in said liquid with the assistance of a substance attached to the polymer. The method is mainly characterized in that the substance attached to the polymer is at least one polypeptide from microorganisms to which polypeptide the Fc-part of the immunoglobulin or its free Fc-fragment can be bonded.

The term "polypeptide" as used here and in the claims also includes proteins, which as known are polypeptides, and the polypeptide may contain carbohydrate units. The term "antigen" as used here and in the claims also includes haptens.

The invention affords a particularly simple, convenient, specific and reversible method of binding immunoglobulins in free form or with their Fab-parts bound to an antigen, to a polymer which is insoluble in said liquid. Since, in accordance with the invention, the immunoglobulin is bound to the polymeric solid phase over its Fc-part, the antigen specific Fab-part is left intact. The Fab-part can thus be bound to an antigen or can be caused to bind itself to an antigen.

The immunoglobulin or its free Fc-fragment to be bonded may derive from different species of animal, primarily vertebrates, preferably mammals. The immunoglobulins may, as is known, belong to different immunoglobulin classes, such as class A (IgA), D(IgD), E(IgE), G(IgG) and M(IgM). The invention is of particular value, since it can be applied in connection with the immunoglobulins belonging to the IgG-class, since, among other things, this class quantitatively dominates the immunoglobulins. The Fc-part of the immunoglobulins can be split off to the corresponding Fc-fragment by known enzymatic methods.

In accordance with the invention, the immunoglobulin or its free Fc-fragment may be unlabelled or labelled. By "labelled" is meant here that the immunoglobulin or its free Fc-fragment is provided with characteristic groups or atoms, such as radioactive atoms or groups containing such or fluorescent groups or one or more substituents having enzymatic activity, for analytical purposes. In a similar manner, the antigen or groups bound thereto may be unlabelled or labelled in the aforementioned manner if the antigen is bound to the Fab-part of the immunoglobulin.

In accordance with another feature of the invention, the relevant polypeptide from microorganisms may be the so-called protein A from Staphylococcus aureus or fragments of said protein, which fragments are of polypeptide nature and are able to bind at least one immunoglobulin at the Fc-part of said immunoglobulin. Said polypeptides (protein A and fragments thereof) deriving from S. aureus can bind immunoglobulins belonging to the IgG-class at their Fc-parts. Other examples are polypeptides from *Staphylococcus epidermidis* and from other bacteria strains.

As mentioned above, the method according to the invention is carried out in the presence of a liquid. The liquid is primarily an aqueous liquid, such as an aqueous buffered common salt solution of appropriate pH, e.g. at approximately the neutral point.

In accordance with the invention, the polypeptide deriving from microorganisms, e.g. the aforementioned protein A or fragments thereof, may be fixed to the polymer by means of bonds of a covalent nature. In this way it is ensured that the polypeptide is not dissolved from the solid phase or removed therefrom during washing operations. The polypeptide may be bound to the polymer by methods conventionally used for binding polypeptides, e.g. proteins, to polymeric substances, e.g. with the assistance of cyanogen halide, isocyanates etc. The insoluble polymeric substances used may be polymers conventionally used for similar purposes, i.e. polymers with functional groups which can be used when binding proteins to polymers. Examples of such functional groups are hydroxyl groups, mercapto groups, primary and secondary amino groups, carbonyl groups, hydrazide groups, diazo groups, and carboxyl groups. These groups can be used when forming bridges by conventional methods from the polymer to a polypeptide, which in this case is a polypeptide from microorganisms such as protein A. The polymer, which is insoluble in the liquid used, may, however, swell in said liquid. For example, it may swell in water when an aqueous liquid is used. The polymer may consist of three-dimensional network, obtained, for example, by cross-linking a polymer such as a polysaccharide. Thus, very different polymers can be used. Cellulose, agarose, polyaminostyrene, cross-linked polymers (for example cross-linked polysaccharides) e.g. dextran cross-linked with epichlorohydrin (Sephadex) or with diepoxides (for example with 1,4-butanediol diglycide ether) or starch or cellulose derivatives or polyvinyl alcohol cross-linked with epichlorohydrin or diepoxides are a few examples of such polymers. Other examples are insoluble polymers obtained by reacting tetraethylenepentamine or hexamethylenediamine with epichlorohydrin or diepoxides. Another example is cross-linked polyacrylamide polymer substituted by p-aminophenyl groups (Enzacryl). The solid phase consisting of polymer may exist in different forms. In many instances, the polymer may have a particulate form. Other examples include a polymeric test tube wall.

The invention also includes an auxiliary agent used when carrying out the method of the invention. This agent is mainly characterized in that it comprises or contains a polymer which is insoluble in the liquid used to carry out the method, to which polymer there is bound at least one polypeptide from microorganisms, said polypeptide being able to bind at least one immunoglobulin at the Fc-part of the latter or its free Fc-fragment.

What has been said in the aforegoing with respect to the method according to the invention is also applicable to the auxiliary agent.

The invention can be applied within different fields when it is required to specifically and — if so desirable — reversibly bind immunoglobulins or their Fc-fragments to a polymeric solid phase. Examples of such applications include purification of an immunoglobulin or its Fc-fragment. Owing to the fact that the immunoglobulin or the Fc-fragment can be bound under mild conditions and then can be separated again under mild conditions, e.g. by changing the pH or ion strength, the immunoglobulin or its Fc-fragment can be obtained in a very pure form. The invention can also be employed for separating one or more immunoglobulins of, for example, class G from remaining immunoglobulin classes in a mixture of different immunoglobulins.

The method of the present invention also renders it possible to specifically bind the Fc-fragments from a mixture of Fc- and Fab-fragments, so that the Fab-fragment can be readily separated in a pure state. The bound Fc-fragment can then be separated from the soluble polymer by a convenient method under mild conditions and is obtained in a pure state.

The method can also be applied in connection with a number of immunological methods for determining immunoglobulins or antigens.

With such methods, the method and auxiliary agent of the present invention can be used to render insoluble immunoglobulins in free or antigen bound form or their Fc-fragments. They can also be labelled in connection herewith.

If the immunoglobulins are bound in free form, their Fab-parts can be used to bind antigens against which these Fab-parts are directed. The antigen may exist in a labelled form. In turn, the antigen may be bound to different groups or substances which may be labelled in accordance with the aforegoing. The invention will now be described with reference to a number of examples.

EXAMPLE 1

I. Preparation of pure protein A from *aureus*

A. Preparing raw extract of protein A from *Staphylococcus aureus*

*S. aureus*, strain Cowan I, cultured in accordance with the recommendations given in European J. Biochem. Vol. 29 (1972) page 572 (Sjöquist et al).

Protein A was released from the bacteria by means of the enzyme preparation lysostaphin. Insoluble material was removed by centrifugation and the liquid phase was recovered. The pH was adjusted to 3.5 with HCl and insoluble material was removed by centrifugation and the liquid recovered. The pH was then adjusted to 7.0 by means of NaOH in accordance with the aforementioned reference.

The liquid obtained represents a raw extract containing protein A in mixture with substances of an impurifying nature.

B. Preparation of agarose with IgG bound thereto

Agarose in the form of a commercially available preparation Sepharose 4 B (Pharmacia Fine Chemicals AB, Uppsala, Sweden) was used in the test.

The agarose was used in the form of minute particles (40 – 190 $\mu$) swollen in water. The particle mass contained 4% be weight of agarose. The particle mass was first washed with water. 100 ml of packed particle mass added with 50 ml water were admixed with 10 g of cyanogen bromide in 50 ml of water whilst stirring at 20°C, the pH being maintained at 10 to 11 by adding 5 normal NaOH. After 10 minutes the particle mass was carefully washed with ice cold water and then with a 0.2 M sodium carbonate-sodium hydrocarbonate buffer in water at pH 9.0 at 4°C.

The cyanogen bromide activated particle mass was slurried in 120 ml of the aforementioned buffer at pH 9.0 containing 3.0 g human IgG (obtained from Kabi AB, Stockholm, Sweden) at 4°C whilst stirring.

After 4 hours the particle mass was removed by filtration and washed with the aforementioned buffer at pH 9.0 and the particle mass was then suspended in 1.5 liters of an aqueous solution containing 0.05 M 2-amino-ethanol and 0.2 M sodium carbonate-sodium hydrogen carbonate at pH 9.0 and stirred at 4°C during 18 hours. The particle mass was then washed with a 0.1 M sodium phosphate buffer in water containing 4 M urea having pH 6.0 and then with a 0.1 M sodium phosphate buffer in water having pH 7.0 until the OD 280 nm of the washing liquid was less than 0.01. The gel mass was then washed with a 0.1 M glycine-HCl buffer in water at pH 3.0 and then again with the aforementioned 0.1 M sodium phosphate buffer having pH 7.0. The obtained product contained approximately 30 mg of bound IgG per 1 ml of packed particle mass.

C. Separation of protein A from raw extract from *S. aureus*

A chromatography column was filled with 100 ml of the packed particle mass having IgG bound thereto with pH 7.0 from sequence B above. 500 ml of the raw extract having pH 7.0 containing protein A from sequence A above was passed slowly through the column with the particle mass at 20°C, the throughflow speed being adjusted to 50 ml per hour. The particle mass was then carefully washed in the column with 0.1 M sodium phosphate buffer in water having pH 7.0 until the OD 280 nm of the washing liquid was less than 0.02. The obtained product contained approximately 3 mg of bound protein A per 1 ml of packed particle mass.

D. Separation of protein A from the particle mass

Protein A bound to the particle mass from sequence C above was released therefrom by eluting the column with 100 ml of 0.1 M glycine-HCl buffer in water at pH 3.0. The collected glycine-HCl buffer containing protein A was dialysed against distilled water, whereafter protein A was obtained in solid form by freeze drying. Approximately 250 mg of protein A were obtained in pure form. (Alternatively, instead of dialysis, desalting can be effected by means of gel filtration.) It could be shown by immunological tests that protein A was free from the substances having an impurifying nature.

II. Preparation of agarose with protein A from *S. aureus* bound thereto

E. Preparation of agarose with protein A bound thereto

Agarose in the form of a commercially available preparation Sepharose 4 B(Pharmacia Fine Chemicals AB, Uppsala, Sweden) was used for the test.

The agarose was used in the form of minute particles (40 – 190 $\mu$) swollen in water. The particle mass contained 4 per cent by weight of agarose. The particle mass was first washed with water. 10 ml of packed particle mass added with 5 ml of water was admixed with 1 g cyanogen bromide in 5 ml water whilst stirring with 20°C, the pH being maintained at 10 to 11 by adding 1 normal NaOH. After 10 minutes, the particle mass was carefully washed with ice cold water and then with a 0.2 M sodium carbonate-sodium hydrogen carbonate buffer in water at pH 9.0 at 4°C.

The cyanogen bromide activated particle mass was slurried in 12 ml of the aforementioned buffer at pH 9.0 containing 50 mg of pure protein A at 4°C whilst stirring.

After 4 hours the particle mass was removed by filtering and washed with the above mentioned buffer at pH 9.0, whereafter the particle mass was suspended in 500 ml of an aqueous solution containing 0.05 M 2-aminoethanol and 0.2 M sodium carbonate sodium hydrogen carbonate having a pH of 9.0 and was stirred at 4°C for 18 hours. The particle mass was then washed with a 0.1 M sodium phosphate buffer in water containing 4 M urea having a pH of 6.0 and then with a 0.1 M sodium phosphate having pH 7.0 until the OD 280 nm of the washing liquid was less than 0.01. The gel mass was then washed with a 0.1 M glycine-HCl buffer in water at pH 3.0 and then again with the aforementioned 0.1 M sodium phosphate buffer at pH 7.0. The obtained product contained about 5 milligrams of bound protein A per ml of packed particle mass.

III. Binding of immunoglobulin from human serum

F. Binding to agarose with protein A bound thereto 10 ml of packed particle mass having bound thereto by covalent bonds protein A from sequence E above with pH 7.0 were introduced to a chromatography column. 10 ml of human serum diluted with 10 ml of the aforementioned 0.1 M sodium phosphate buffer having a pH of 7.0 was slowly passed through the column with the particle mass at 20°C, the throughflow time being 30 minutes. The particle mass was then thoroughly washed in the column with 0.1 M sodium phosphate buffer in water at pH 7.0 until the OD 280 nm of the washing liquid was less than 0.02. The obtained product contained immunoglobulins belonging to the IgG class bound to the particle mass.

The bound immunoglobulins can be released from the polymer particles by simple processes, e.g. by changing the pH or ion strength. Thus, the immunoglobulins bound in accordance with the aforedescribed technique were reseparated from the particle mass by elution with a 0.1 M glycine-HCl buffer in water with pH 3.0. It was established by immunological tests etc. that the liberated immunoglobulins were pure from remaining serum proteins and belonged to the immunoglobulin class IgG.

EXAMPLE 2

Binding of immunoglobulin from pig serum

The test was carried out in a manner similar to that disclosed in Example 1. In this instance, however, the particle mass with protein A seated thereon was not introduced to a column, but that the immunoglobulin was bound in the following manner: 10 ml of the packed particle mass with protein A covalently bound thereto (the protein A being obtained analogous with sequence E in Example 1) were suspended in 50 ml of 0.1 M sodium phosphate buffer in water at a pH of 7.0. 10 ml of pig serum were added dropwise for 10 minutes at a temperature of 20°C. After 30 minutes the particle mass was separated by filtration and carefully washed with 0.1 M sodium phosphate buffer in water at a pH of 7.0. Similar to Example 1, the immunoglobulins belonging to the IgG-class had been bound to the particle mass. This could be shown after separating bound immunoglobulins and subsequent analyses in a manner analogous with that described in Example 1.

EXAMPLE 3

I. Preparation of polypeptide

A. preparation of raw extract of polypeptide fragment of protein A from Staphylococcus aureus S. aureus, strain Cowan I, were cultured in accordance with recommendations given in European J. Biochem, Vol. 29 (1972), page 572 (Sjöquist et al).

The bacteria were removed by centrifuging and washed with 0.9 per cent NaCl solution in water. 100 g of bacteria (wet weight) were slurried in 150 ml of a physiological common salt solution. 10 mg of trypsin (free from chymotrypsin) were added thereto. The pH was 7.2. The enzyme treatment process was effected at 30°C at pH 7.2 during 30 minutes, whereafter 20 mg of trypsin inhibitor from soya beans were added. The suspension was then centrifuged. The supernatant liquid was recovered and sterile filtered through Millipore filters.

The sterile filtered liquid contains fragments of protein A of a polypeptide character, in mixture with substances of an impurifying character. For the purpose of purifying the fragments capable of binding itself to the Fc-part of the IgG-molecules they were isolated with the aid of agarose having IgG bound thereto.

B. Preparation of agarose with IgG bound thereto

Human IgG was bound to agarose as described in example 1, part B, above.

C. Separation of polypeptide fragments of protein A from S. aureus

A chromatography column was filled with 100 ml of the packed particle mass with IgG bound thereto with pH 7.0 from sequence B above. 100 ml of the raw extract of pH 7.0 containing polypeptide fragments from protein A from sequence A above was passed slowly through the column with the particle mass at 20°C, the throughflow speed adjusted to 50 ml per hour. The particle mass was then carefully washed in the column with 0.1 M sodium phosphate buffer in water at pH 7.0 until the OD 280 nm of the washing liquid was less than 0.02. The obtained product contained approximately 1 mg of bound polypeptides per 1 ml of packed particle mass.

D. Separation of polypeptide fragments of protein A from the particle mass

The polypeptides bound to the particle mass from sequence C above were released from the particle mass by eluting the column with 100 of 0.1 M glycine-HCl buffer in water with a pH of 3.0. The collected glycine-HCl buffer containing the polypeptides capable of binding the Fc-part of IgG-molecules, was desalted by gel filtration with the assistance of Sephadex G25 (particles of dextran cross-linked with epichlorohydrin). Approximately 100 mg of polypeptides having a molecular weight of approximately 7000 were isolated by freeze drying. It could be shown by chromatography that the polypeptide fraction contained several closely related polypeptides, all having said ability of binding the Fc-parts of IgG-molecules. By, inter alia, immunological tests it could be shown that the polypeptide fraction was pure from substances of a contaminating nature.

In a corresponding manner, polypeptide fragments capable of binding the Fc-part of IgG-molecules can be isolated by first isolating protein A and then treating protein A in solution at, e.g., pH 8.2 with trypsin in a manner analogous with the foregoing, whereafter the polypeptide fragments having the relevant properties are separated in a manner corresponding to that described above by binding the same to agarose with IgG bound thereto and then separating the polypeptide fragments.

II. Preparation of agarose with polypeptide from protein A from *S. aureus* bound thereto E. Preparation of agarose with polypeptide bound thereto Agarose in the form of a commerically available preparation Sepharose 4 B (Pharmacia Fine Chemicals AB, Uppsala, Sweden) was used for the method.

The agarose was used in the form of minute particles (40 – 190μu) swollen in water. The particle mass contained 4 percent by weight of agarose. The particle mass was first washed with water. 10 ml of packed particle mass added with 5 ml water was admixed with 1 g cyanogen bromide in 5 ml water whilst stirring at 20°C, the pH being maintained at 10 to 11 by adding 1 -normal NaOH. After 10 minutes, the particle mass was carefully washed with ice cold water and then with a 0.2 M sodium carbonate-sodium hydrogen carbonate buffer in water at pH 9.0 at 4° C.

The cyanogen bromide activated particle mass was slurried in 12 ml of the aforementioned buffer at pH 9.0 containing 25 mg of pure polypeptide at 4°C whilst stirring.

After 4 hours the particle mass was removed by filtering and washed with the above mentioned buffer at pH 9.0, whereafter the particle mass was suspended in 500 ml of an aqueous solution containing 0.05 M 2-aminoethanol and 0.2 M sodium carbonate-sodium hydrogen carbonate having a pH of 9.0 and was stirred at 4°C for 18 hours. The particle mass was then washed with a 0.1 M sodium phosphate buffer in water containing 4 M urea having a pH of 6.0 and then with a 0.1 M sodium phosphate buffer in water having pH 7.0 until the OD 280 nm of the washing liquid was less than 0.01. The gel mass was then washed with a 0.1 M glycine-HCl buffer in water at pH 3.0 and then again with the aforementioned 0.1 M sodium phosphate buffer at pH 7.0. The obtained product contained bound polypeptide capable of binding the Fc-part of IgG-molecules.

III. Binding of immunoglobulin from human serum

F. Binding to agarose with polypeptide bound thereto 10 ml of packed particle mass having bound thereto by covalent bonds a polypeptide from sequence E above with pH 7.0 were introduced to a chromatography column, 10 ml of human serum diluted with 10 ml of the aforementioned 0.1 M sodium phosphate buffer having a pH of 7.0 was slowly passed through the column with the particle mass at 20°C, the throughflow time being 30 minutes. The particle mass was then thoroughly washed in the column with 0.1 M sodium phosphate buffer in water at pH 7.0 until the OD 280 nm of the wasing liquid was less than 0.02. The obtained product contained immunoglobulins belonging to the IgG class bound to the particle mass.

The bound immunoglobulins can be released from the polymer particles by simple processes, e.g. by changing the pH or ion strength. Thus, the immunoglobulins bound in accordance with the aforedescribed technique were separated from the particle mass by elution with a 0.1 M glycine buffer in water at pH 3.0. It was established by immunological tests etc. that the reliberated immunoglobulins were pure from remaining serum proteins and belonged to the immunolobulin class IgG.

EXAMPLE 4

Binding of immunoglobulin from pig serum

The test was carried out in a manner similar to that disclosed in Example 3. In this instance, however, the particle mass with polypeptide seated thereon was not introduced to a column, but that the immunoglobulin was bound in the following manner: 10 ml of the packed particle mass with polypeptide covalently bound thereto (the polypeptide being obtained analogous with sequence E in Example 3) were suspended in 50 ml of 0.1 M sodium phosphate buffer in water at a pH of 7.0. 10 ml of pig serum were added dropwise for 10 minutes at a temperature of 20°C. After 30 minutes the particle mass was separated by filtration and carefully washed with 0.1 M sodium phosphate buffer in water at a pH of 7.0. Similar to Example 3, the immunoglobulins belonging to the IgG-class had been bound to the particle mass. This could be shown after separating bound immunoglobulins and subsequent analyses in a manner analogous with that described in Example 3.

In a similar way as in the above examples insoluble particles of dextran cross-linked with epichlorohydrin (Sephadex) and cellulose were used instead of agarose giving similar results.

What I claim is:

1. In the method of binding, in the presence of an aqueous liquid, at least one immunoglobulin or its free Fc-fragment to a polymer insoluble in said aqueous liquid with the assistance of a substance attached to the polymer by contacting said polymer with the substance attached thereto with said immunoglobulin or its free Fc-fragment in the aqueous liquid, the improvement which comprises using at least one polypeptide from Staphylococci as said substance attached to said polymer, said immunoglobulin being from the IgG-class and said polypeptide being able to bind at least one immunoglobulin from the IgG-class at the Fc-part of the said immunoglobulin.

2. The method according to claim 1, wherein said immunoglobulin is from vertebrates.

3. The method according to claim 2, wherein said immunoglobulin is from mammals.

4. The method according to claim 1, wherein said immunoglobulin or its free Fc-fragment is labelled.

5. The method according to claim 4, wherein the labelled immunoglobulin or the Fc-fragment is labelled by means of an enzyme or a radioactive or fluorescent atom or group.

6. The method according to claim 1 wherein an antigen is bound to the Fab-part of said immunoglobulin.

7. The method according to claim 6, wherein said antigen is labelled.

8. The method according to claim 7, wherein the labelled antigen is labelled by means of an enzyme or a radioactive or fluorescent atom or group.

9. The method according to claim 1 wherein the polypeptide is attached to the polymer by means of bonds of a covalent nature.

10. The method according to claim 1, wherein the polymer is in particulate form.

11. The method according to claim 1, wherein the polypeptide is protein A from Staphylococcus aureus or fragments thereof, said fragments being of poltypeptide nature and being able to bind at least one immunoglobulin from the IgG-class at the Fc-part of said immunoglobulin.

* * * * *

REEXAMINATION CERTIFICATE (522nd)
United States Patent [19]
Sjöquist

[11] B1 3,995,018
[45] Certificate Issued  Jun. 24, 1986

[54] METHOD OF BINDING IMMUNOGLOBULIN EMPLOYING A POLYPEPTIDE FROM MICROORGANISMS

[75] Inventor: John A. Sjöquist, Upsala, Sweden

[73] Assignee: Pharmacia Aktiebolag, Upsala, Sweden

Reexamination Request:
No. 90/000,807, Jun. 27, 1985

Reexamination Certificate for:
Patent No.: 3,995,018
Issued: Nov. 30, 1976
Appl. No.: 409,572
Filed: Oct. 25, 1973

[30] Foreign Application Priority Data

Nov. 6, 1972 [SE]  Sweden ............................. 14330/72
Feb. 8, 1973 [SE]  Sweden .............................. 7301779

[51] Int. Cl.$^4$ .................. G01N 33/53; G01N 33/563; G01N 33/544; G01N 33/545
[52] U.S. Cl. ........................................ 435/7; 436/518; 436/528; 436/531; 436/532; 436/541; 436/800; 436/804; 436/823; 436/512; 436/824; 436/828; 436/519; 436/513; 436/529; 436/530; 436/826; 260/112 R; 424/88; 424/1.1
[58] Field of Search ............... 436/512, 528, 531, 532, 436/800, 804, 828; 435/7

[56] References Cited

PUBLICATIONS

"'Protein A' from *S. aureus*," Forsgren, A. and Sjoquist, J. (1966) *The Journ. of Immun.* 97, 822–827.
"Protein A from *Staphylococcus aureus*," Sjoquist, J. and Stalenheim, G. (1969) *The Journ of Immun.* 103, 467–473.
"Protein A Isolated from *Staphylococcus aureus* After Digestion with Lysostaphin," Sjoquist, J., Meloun, B. and Hjelm, H. (1972) *Eur. J. Biochem.* 29, 572–587.
"Water-Insoluble Derivatives of Enzymes Antigens, and Antibodies," Silman. I. and Katchalski, E. (1966) *Ann. Rev. of Biochem.* 873–908.
"Immunologic Adsorbents," Campbell, D., Luescher, E. and Lerman, L. (1951) *Proc. N.A.S.* 37, 575–578.
"The Use of Affinity Chromatography for the Specific Purification of Antibodies and Antigens," Wofsy, L. and Burr, B. (1969) *The Journ. of Immun.* 103, 380–382.
"Protein A from *Staphylococcus aureus*," Forsgren, A. and Sjoquist, J. (1969) *Acta Path. Microbiol. Scandinav.* 75, 466–480.
"Studies of Antigen Preparations from *Staphylococcus aureus*," Grov. A. (1968) *Acta Path. Microbiol. Scandinav.* 73, 400–406.
"Quantitation of Staphylococcal Protein A: Determination of Equilibrium Constant and Number of Protein A Residues on Bacteria," Kronvall, G., Quie, P., and Williams, Jr., R. (1970), *The Jour. of Immunol,* 104, 273–278.

Primary Examiner—Christine M. Nucker

[57] ABSTRACT

A method of binding, in the presence of a liquid, at least one immunoglobulin or its free Fc-fragment, the immunoglobulin being in free form or with its Fab-part bound to an antigen to which is optionally in turn bound one or more groups or substances, to a polymer insoluble in said liquid with the assistance of a substance attached to the polymer. The substance used is at least one polypeptide from microorganisms to which polypeptide the Fc-part of the immunoglobulin or its free Fc-fragment can bind itself.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-11 is confirmed.

* * * * *

REEXAMINATION CERTIFICATE (715th)
United States Patent [19]

Sjöquist

[11] B2 3,995,018

[45] Certificate Issued    Jul. 7, 1987

[54] METHOD OF BINDING IMMUNOGLOBULIN EMPLOYING A POLYPEPTIDE FROM MICROORGANISMS

[75] Inventor: John A. Sjöquist, Uppsala, Sweden

[73] Assignee: Pharmacia Aktiebolag, Uppsala, Sweden

Reexamination Request:
No. 90/001,075, Aug. 27, 1986

Reexamination Certificate for:
Patent No.: 3,995,018
Issued: Nov. 30, 1976
Appl. No.: 409,572
Filed: Oct. 25, 1973

Reexamination Certificate B1 3,995,018 issued Jun. 24, 1986.

[30] Foreign Application Priority Data

Nov. 6, 1972 [SE] Sweden ............................ 14330/72
Feb. 8, 1973 [SE] Sweden ............................ 7301779

[51] Int. Cl.[4] .................. G01N 33/53; G01N 33/563; G01N 33/544; G01N 33/545
[52] U.S. Cl. ......................................... 435/7; 424/11; 424/88; 436/512; 436/513; 436/518; 436/519; 436/528; 436/529; 436/530; 436/531; 436/532; 436/541; 436/800; 436/804; 436/823; 436/824; 436/826; 436/828; 530/388; 530/389; 530/391; 530/806; 530/814; 530/816; 530/825
[58] Field of Search ............... 436/512, 528, 531, 532, 436/800, 804, 828; 435/7; 530/388, 389, 391, 825, 806, 814, 816

[56] References Cited
PUBLICATIONS

Cuatrecasas, et al., "Selective Enzyme Purification by Affinity Chromatography", *Biochemistry 61*, (1968), 636–643.

Cuatrecasas, "Protein Purification by Affinity Chromatography", *J. Biol. Chem.* 245, (1970), 3059–3065.

Cuatrecasas, et al., "Affinity Chromatography", *Methods in Enzymology 22*, (1971), 345–378.

Cuatrecasas, "Selective Adsorbents Based on Biochemical Specificity" *Biochemical Aspects of Reactants on Solid Supports*, (1971), Stark, Ed., Academic Press, N.Y., pp. 79–109.

Cuatrecasas, "Affinity Chromatography of Macromolecules", (1972) *Adv. in Enzymology 36*, 29–89.

Kronvall, et al., "Quantitation of Staphylococcal Protein A: Determination of Equilibrium Constant and Number of Protein A Residues on Bacteria", (1970), *J. Immunol.* 104, 273–278.

*Primary Examiner*—Christine M. Nucker

[57] ABSTRACT

A method of binding, in the presence of a liquid, at least one immunoglobulin or its free Fc-fragment, the immunoglobulin being in free form or with its Fab-part bound to an antigen to which is optionally in turn bound one or more groups or substances, to a polymer insoluble in said liquid with the assistance of a substance attached to the polymer. The substance used is at least one polypeptide from microorganisms to which polypeptide the Fc-part of the immunoglobulin or its free Fc-fragment can bind itself.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-11 is confirmed.

* * * * *